US005740909A

United States Patent [19]
Nazare et al.

[11] Patent Number: 5,740,909
[45] Date of Patent: Apr. 21, 1998

[54] LOCKABLE AND LEAK-PROOF SHARPS DISPOSAL CONTAINER

[75] Inventors: Raymond Nazare; Donna M. Nazare, both of Woodland Hills; William L. Gottsegen, Encino, all of Calif.

[73] Assignee: Gene W. Arant, Ventura, Calif.; a part interest

[21] Appl. No.: 795,507

[22] Filed: Feb. 10, 1997

Related U.S. Application Data

[63] Continuation-in-part of Ser. No. 535,971, Sep. 29, 1995, Pat. No. 5,603,404.

[51] Int. Cl.$^6$ .................................................. B65F 1/16
[52] U.S. Cl. ........................... 206/366; 206/1.5; 220/254; 220/908
[58] Field of Search .............................. 206/365, 366, 206/1.5; 220/481, 254, 908

[56] References Cited

U.S. PATENT DOCUMENTS

| | | | |
|---|---|---|---|
| 4,715,498 | 12/1987 | Hanifl | 206/366 |
| 5,046,614 | 9/1991 | Torres et al. | 206/366 |
| 5,154,345 | 10/1992 | Shillington | 206/366 |

*Primary Examiner*—Jacob K. Ackun
*Attorney, Agent, or Firm*—Gene W. Arant

[57] ABSTRACT

A sharps container has a receptacle, cover and tray and provides an improved locking mechanism to resist unauthorized tampering, as well as hermetically sealed construction to prevent any leakage of fluids from the container. The rotating tray provides an escapement mechanism for hands-free disposal of sharps through biasing the offset balanced tray into an open, receiving position to receive new items and deposit them into the interior of the container, and then returning to a nearly closed position. A locking mechanism is also provided to rotate the tray into a locking position thereby permanently closing the container and displacing the locking mechanism into the container interior so that the top surface of the locking mechanism is flush with the adjacent exterior container surface.

18 Claims, 8 Drawing Sheets

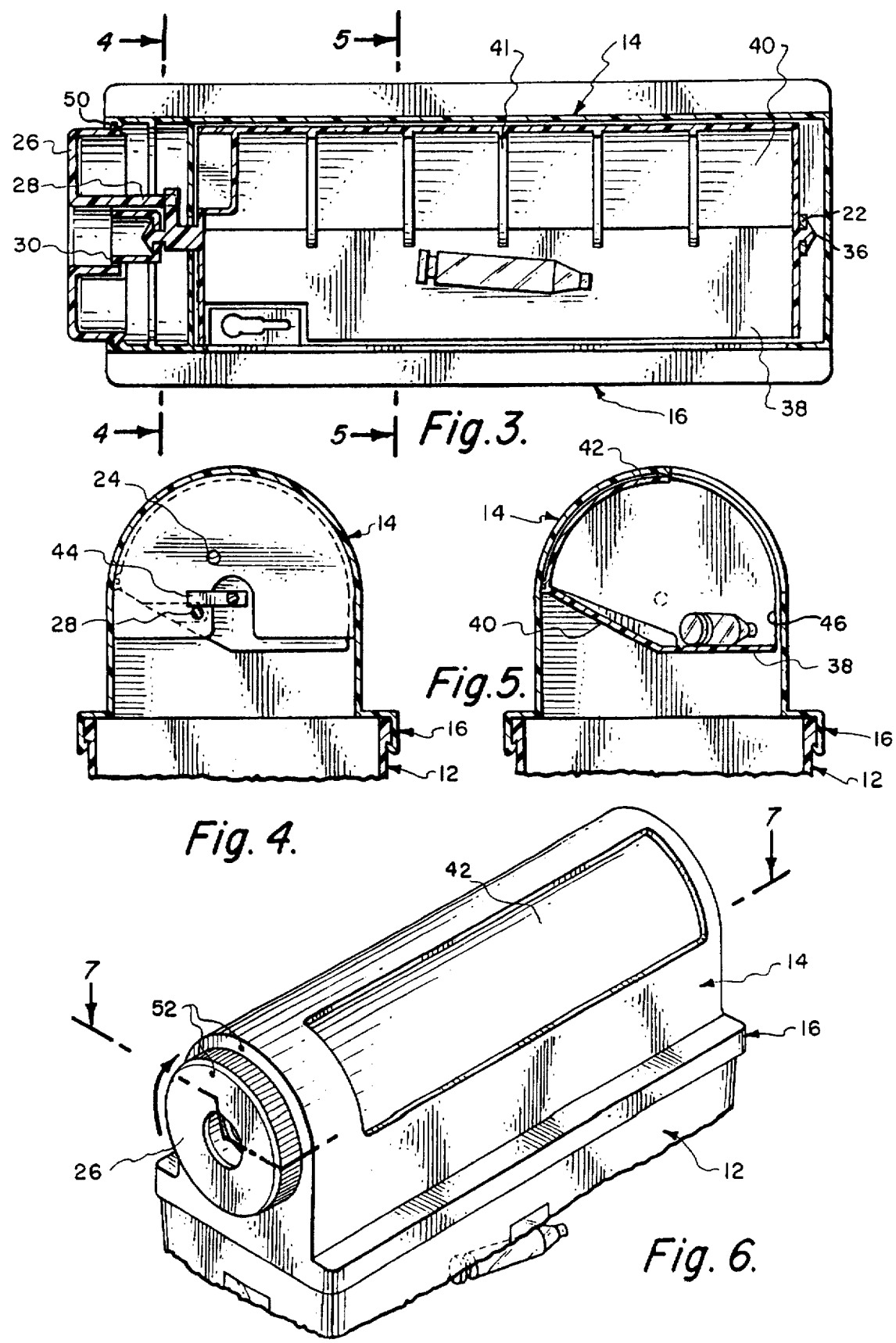

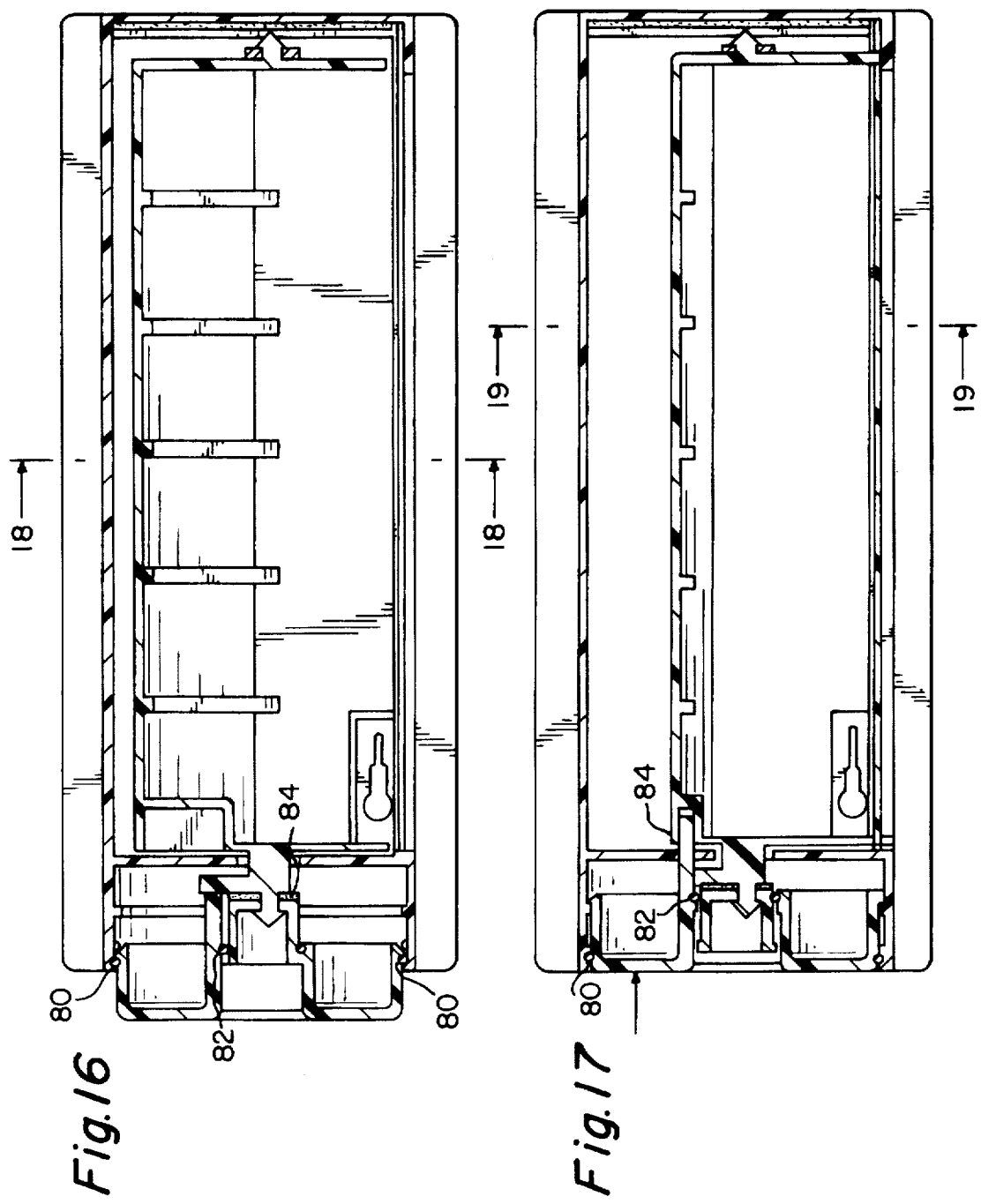

LOCKABLE AND LEAK-PROOF SHARPS DISPOSAL CONTAINER

RELATED APPLICATION

This application is a continuation-in-part of our prior application Ser. No. 08/535,971 filed Sep. 29, 1995, now U.S. Pat. No. 5,603,404.

BACKGROUND OF THE INVENTION

This invention relates to a sharps disposal container, i.e. an apparatus for disposing of sharp items such as hypodermic needles and syringes used in hospitals. Many hospitals require and various government agencies recommend that a separate sharps disposal container be placed in each patient and emergency room. Such policy promotes the quick and efficient disposal of used syringes and other sharp items thereby diminishing the chances of potential injury or infection caused by these items to patients or hospital staff. When the disposed material within the container reaches a determined level, the container can be first permanently locked and thereafter removed from the hospital room and disposed.

With the present concerns surrounding an accidental transmittal of the HIV virus and syringe reuse by intravenous drug users, a typical sharps disposal container is designed not only to permit disposal but also to prevent theft of any objects deposited therein. Because of the trend toward placement of sharps disposal containers in each patient's room as discussed above, it is an important consideration to manufacture these containers at an economical price while providing an appropriate level of protection to patients, hospital staff and other individuals alike.

PRIOR ART

Pertinent prior art includes U.S. Pat. Nos. 4,828,107 issued to Spencer in 1989; 5,154,345 issued to Shillington in 1992; and U.S. Pat. No. 5,395,008 issued to Bemis et al in 1995.

These prior patents show sharps containers having a covered receptacle within whose cover there is a receiving or "dump" tray that is accessible through an opening in the cover and is pivotal about its longitudinal axis for allowing objects placed upon it to drop into the interior of the receptacle.

SUMMARY OF THE INVENTION

The present invention addresses the above mentioned concerns and provides a sharps disposal unit that provides hands-free operation for depositing objects within the unit, is puncture resistant, and provides a novel locking mechanism for permanently and irreversibly locking the unit to prevent retrieval of disposed material contained within. Further, the invention in its preferred form provides a system of sealing mechanisms that securely and hermetically seal the container when in its locked position, so that any liquid material that may escape from a syringe or the like into the interior of the container will be securely retained there. Thus, not only are the items to be disposed of securely locked within the interior of the container, but no contaminated liquid can leak out of the interior of the container.

According to the presently preferred form of the apparatus, the invention provides a sharps disposal container having a receptacle and a cover, and a permanent interlocking means such that when once assembled, the cover cannot be separated from the receptacle. An opening in the cover is configured to permit disposal of a syringe or similar shaped objects only by horizontal placement onto a tray in a "hands-free" operation. Obtaining hand access to the interior of the container is essentially impossible. An object placed horizontally on the tray and thereafter displaced into the receptacle will tend to remain in a horizontal position after displacement. The displaced objects will then tend to be stacked uniformly thereby permitting a more efficient usage of the receptacle interior.

The unique locking means of the invention includes a dial assembly that is rotatable and moveable for controlling the locking operation. When the container is to be disposed of, the dial assembly is used to rotate the tray and an associated sliding door member into a locking position. At the same time, a locking pin that is part of the dial assembly is displaced into an aperture disposed in the cover, thus preventing any rotation of the tray back to an open position. Thereafter, the dial assembly is forced longitudinally into the cover so that its top exterior surface is substantially flush with the adjacent outside surface of the cover.

Thus the objects of the invention are to provide a sharps disposal container that requires only a "hands free" operation, prevents retrieval of items disposed therein, can be securely and irreversibly locked when it is filled, and has a hermetically sealed interior so as to prevent leakage of fluids from its interior.

DESCRIPTION OF THE DRAWINGS

FIGS. 1 through 5 show the invention with receiving tray in open position; FIG. 1 being a perspective view of the invention, FIG. 2 an exploded perspective view, FIG. 3 a longitudinal cross-section view of cover and tray on line 3—3 in FIG. 1, FIG. 4 a transverse cross-section view on line 4—4 in FIG. 3, and FIG. 5 a transverse cross-section view on line 5—5 in FIG. 3;

FIGS. 6 through 9 show the invention having the tray rotated by the dial into locking position; FIG. 6 being a perspective view of the cover, FIG. 7 a longitudinal cross-section view on line 7—7 in FIG. 6, FIG. 8 a transverse cross-section on line 8—8 in FIG. 7, and FIG. 9 a transverse cross-section view on line 9—9 in FIG. 7;

FIG. 10 being a perspective view of the cover, FIG. 11 a longitudinal cross-section view on line 11—11 in FIG. 10, FIG. 12 a transverse cross-section view on line 12—12 in FIG. 11, and FIG. 13 a transverse cross-section view on line 13—13 in FIG. 11;

FIGS. 14 through 20 show the hermetic sealing details;

FIG. 14 being a perspective view of the cover with receiving tray in open position, and also showing the sealing means for the rotating tray; FIG. 16 taken on line 16—16 in FIG. 14 being a longitudinal cross-section of the cover with tray in open position; and FIG. 18 taken on line 18—18 of FIG. 16 being a transverse cross-section of the cover with tray in open position;

FIG. 15 being a perspective view of the cover with the tray in its closed position, and the cover being partially cutaway to show the sealing means between tray and cover; FIG. 17 taken on line 17—17 in FIG. 15 being a longitudinal cross-section of the cover with tray in the closed position; FIG. 19 taken on line 19—19 of FIG. 17 being a transverse cross-section with the cover closed; and FIG. 20 is a longitudinal cross-section plan view taken on line 20—20 of FIG. 18 showing the sealing means between the bottom of the cover and the top of the receptacle.

DETAILED DESCRIPTION OF THE PREFERRED EMBODIMENT

The preferred embodiment of the invention comprises a disposal container having a main receptacle, a cover mounted on the top of the receptacle, and a rotatable tray that cooperates with an opening in the cover to permit disposal items to be dropped into the container. The tray is normally in an open or receiving position, and when an object such as a syringe is to be disposed of, it is dropped onto the tray, which then rotates temporarily so as to cause the object to drop downward into the main receptacle. The tray then returns automatically to its normal position.

According to the present invention, when the container is full, or is for some other reason to be disposed of, a novel locking mechanism is then used to securely and permanently lock it so that its contents cannot be removed. The locking mechanism includes a dial assembly that is hand-operated to rotate the tray into a predetermined position, and the dial assembly is then forced longitudinally toward and into the cover so as to securely lock the dial assembly, tray, and cover together.

The container, escapement, and novel locking mechanism have been disclosed in our prior copending application, now U.S. Pat. No. 5,603,404, in drawing FIGS. 1 through 14 thereof, and are again shown in the corresponding drawing figures of the present application. A significant improvement that is disclosed herein is a system of sealing mechanisms that securely and hermetically seal the container. These novel features are shown in drawing FIGS. 14 through 20. Thus, any liquid material that may escape from a syringe or the like into the interior of the container will be securely retained there. This feature is of critical importance to the medical industry, since it is imperative not only that items to be disposed of are securely locked within the interior of the container, but that no contaminated liquid can leak out of the interior of the container.

The invention will first be described with reference to drawing FIGS. 1 through 13. The sealing means will then be described with reference to FIGS. 14 through 20, in which minor but significant changes in the structure of the container are shown.

Figure 1:
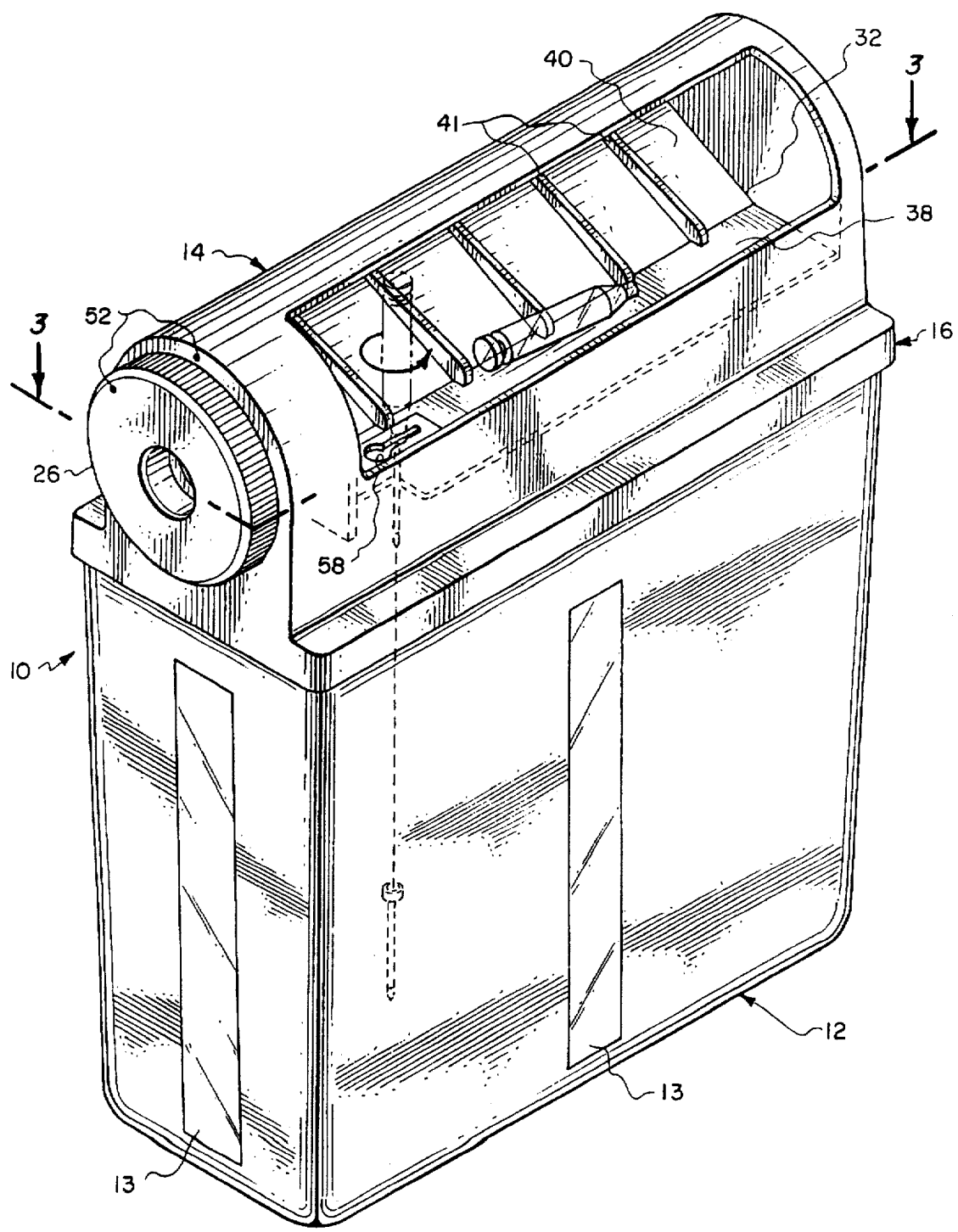

FIG. 1 illustrates the overall structure of the sharps container 10 of this invention. Its principal subassemblies are receptacle and cover; rotating tray; and dial assembly.

Receptacle and Cover

The container 10 includes a receptacle 12 made of a puncture resistant material, and a cover 14 made of a similar material. Cover 14 is of a horizontally extending, generally semi-cylindrical configuration, and has a horizontal base 16 for attachment to the top of receptacle 12. As shown in FIG. 4, the base 16 and the upper perimeter of receptacle 12 are provided with interlocking edges so that once assembled, the receptacle and its cover are permanently locked together and the receptacle cannot be separated from the cover.

The receptacle 12 has viewing windows 13 made of a puncture resistant material on three of its sidewalls to permit visual observation of the disposed material present within container 10. Container 10 is designed to be attached to a wall by the use of mounting brackets, not shown, with a particular sidewall that does not incorporate a viewing window 13 being attached to the mounting wall.

Figure 2:
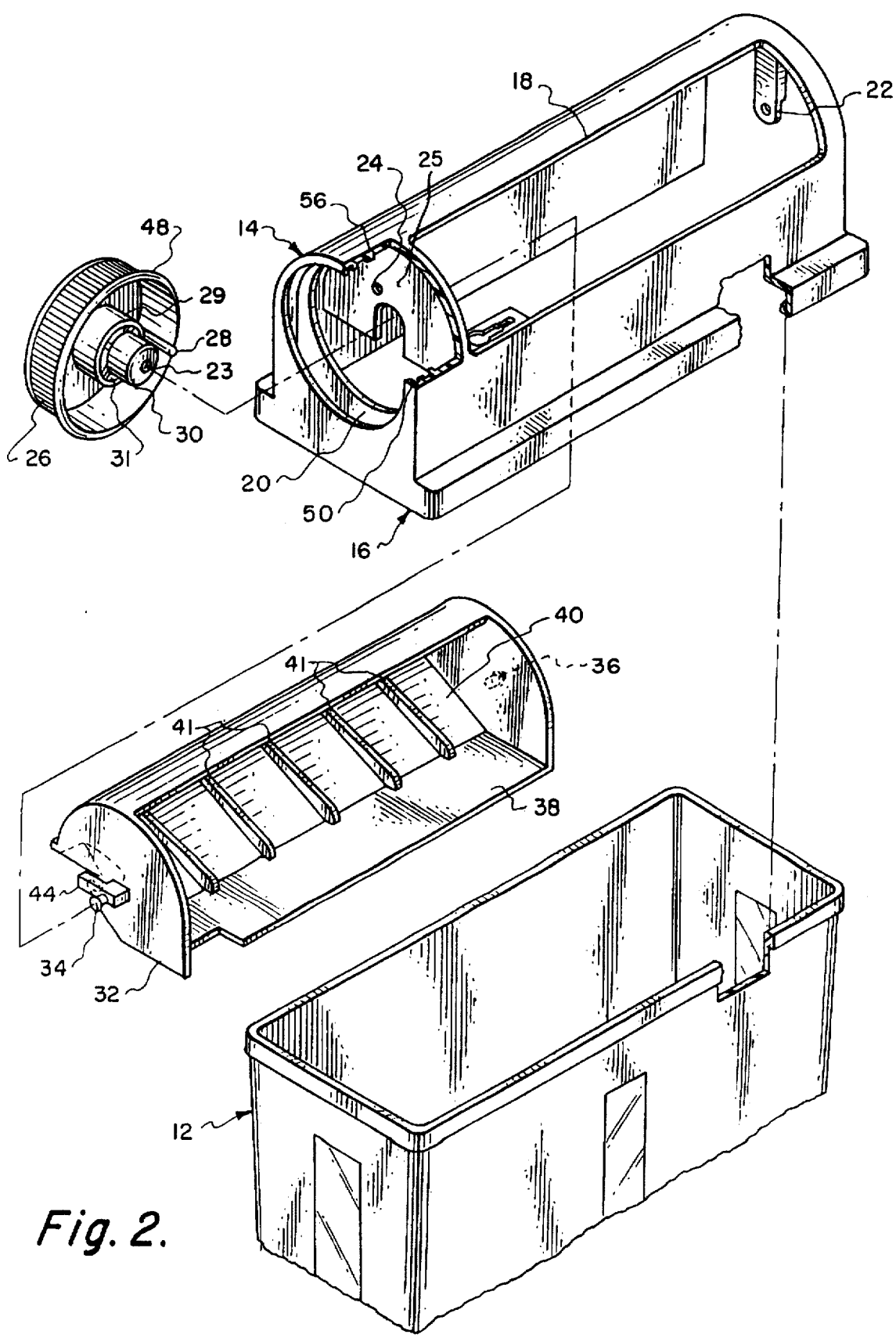

The cover 14 has an opening 18 formed in an upper side wall which allows access to an elongated tray 32. The opening 18 can be of any geometrical configuration and area which would permit the easy disposition of a syringe onto the tray, but is preferably made in a generally rectangular shape, as best shown in FIGS. 1 and 2. The opening 18 in the cover 14 is configured to permit disposal of a syringe or similar shaped objects only by horizontal placement onto a tray 32.

Figure 7:
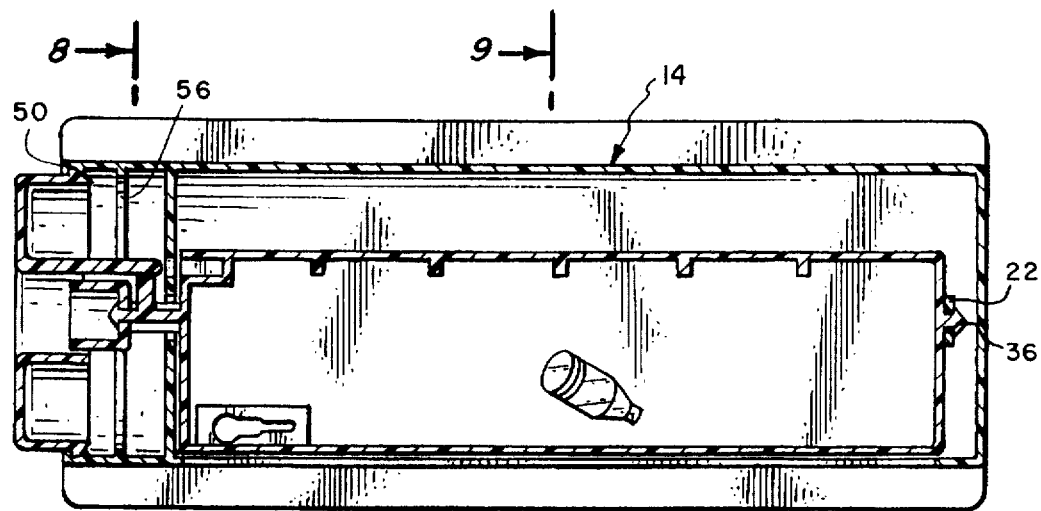
Figures 8, 9:
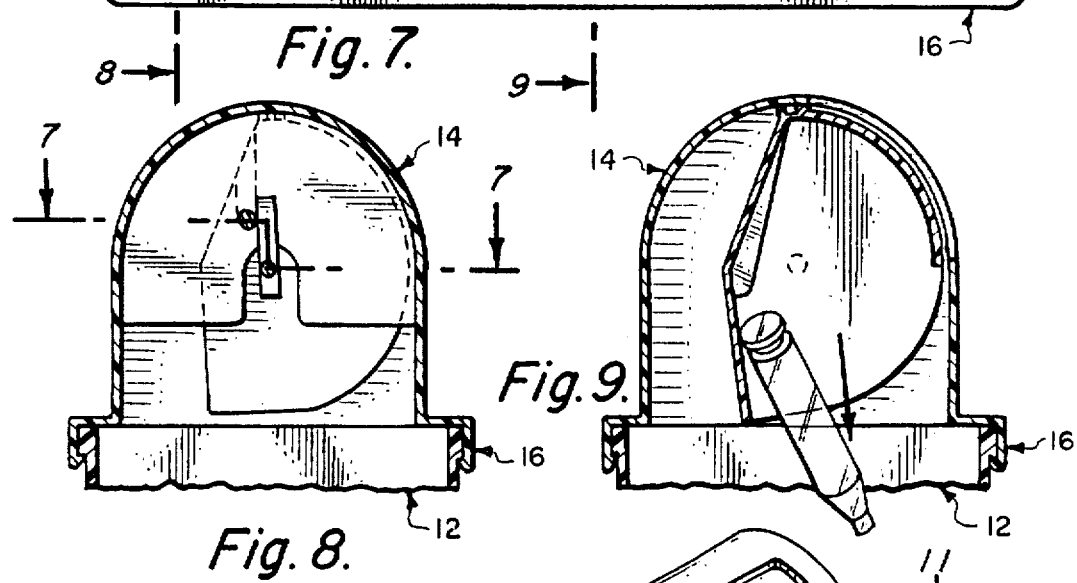

A dial recess 20 is formed in one end of the cover, and has first and second inwardly extending circumferential shoulders. The first or outer shoulder 50, best shown in FIGS. 2, 3, and 7, is formed near the outer extremity of the interior wall surface of the dial recess 20. This shoulder permits insertion of the dial assembly into the dial recess but prevents its retraction or removal in the opposite direction. The second or inner shoulder 56 is best shown in FIGS. 2, 3, 7, and 11, and is utilized to retain the dial assembly in its inserted or locked position.

Figure 11:
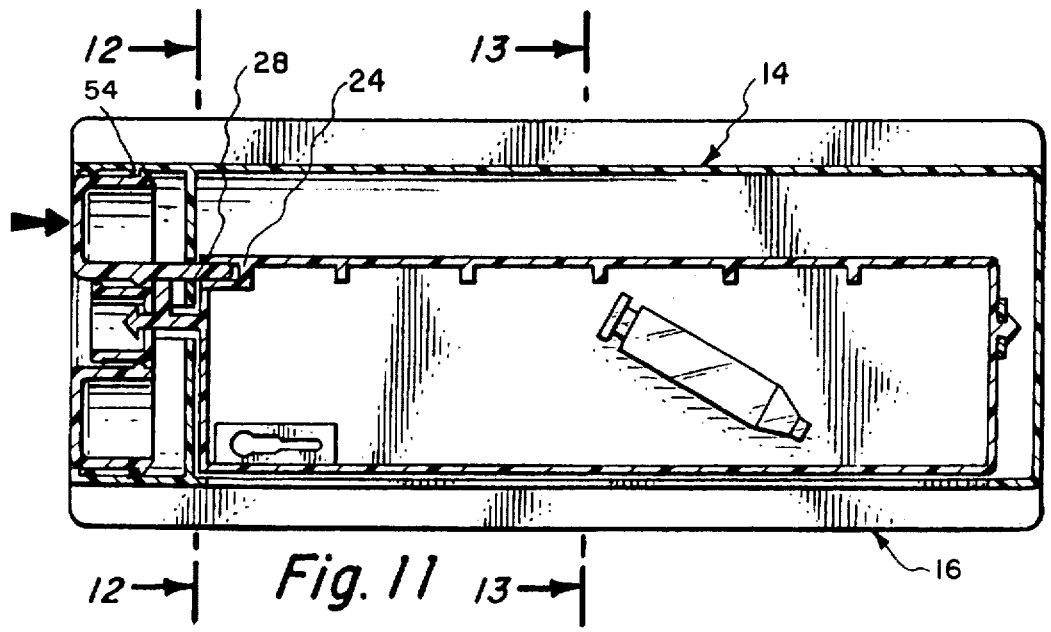
Figures 12, 13:
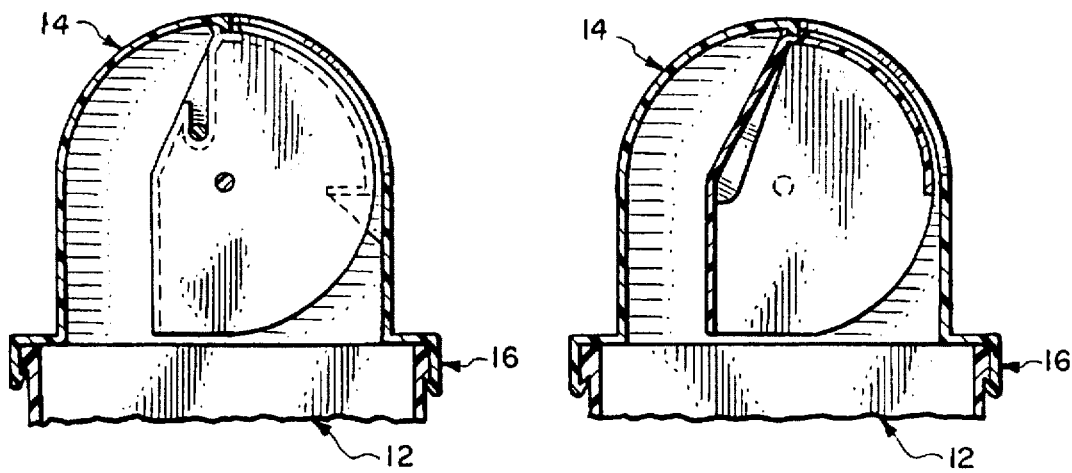
Figure 14:
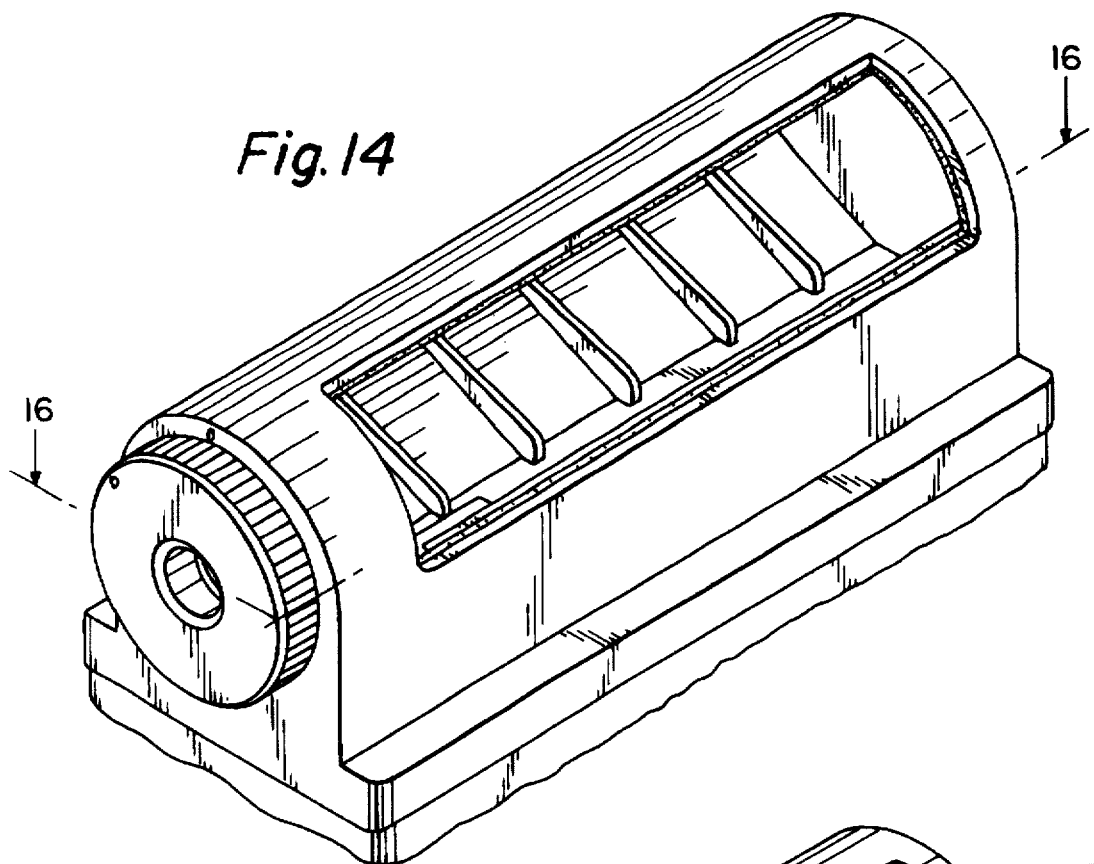
Figure 15:
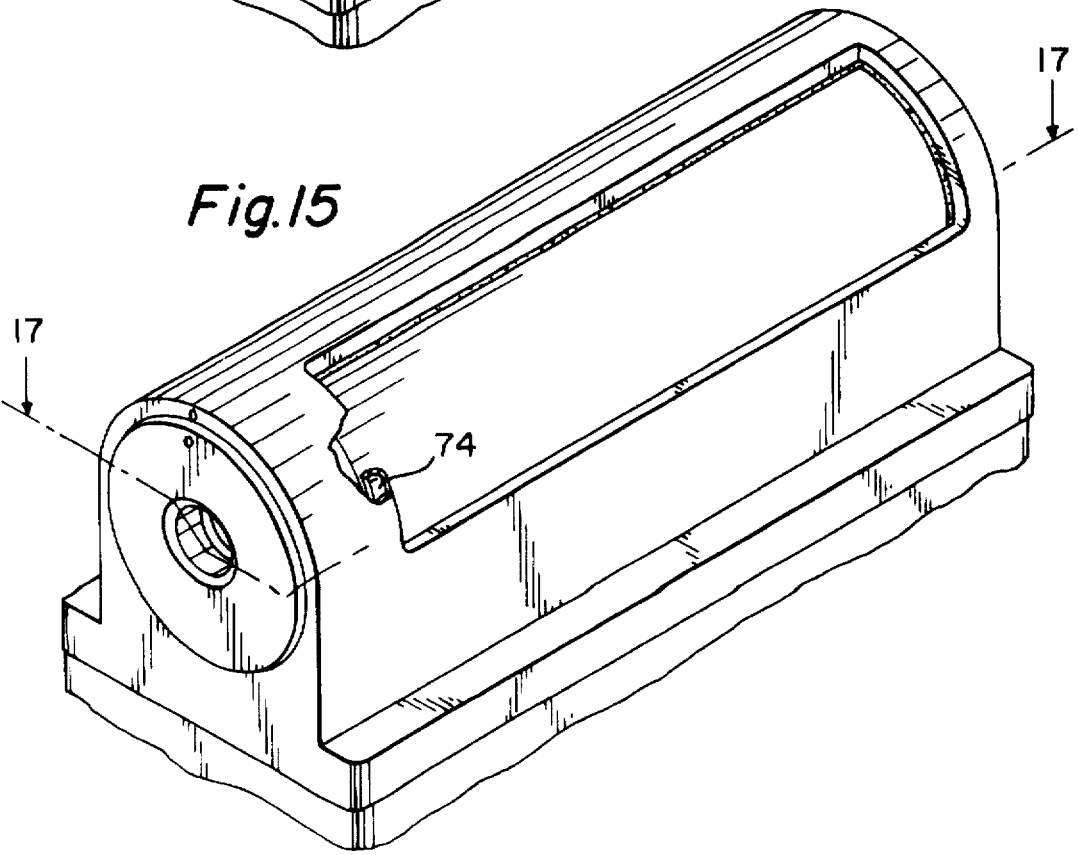

On the interior side of the remote end wall of cover 14 as shown in FIG. 2 is a pivot pin recess 22, also shown in FIGS. 3, 7, and 11. This recess supports a pin 36 that protrudes from the far end of the tray 32, shown in dotted lines in FIG. 1 and best seen in FIGS. 3, 7, and 11. An internal vertical wall 25 separates dial recess 20 from the remaining cover interior, and there is a locking pin aperture 24 located at the base of the dial recess 20 in wall 25. The aperture 24 is utilized only when inserting the dial assembly into its fully locked position.

An internal wall surface portion 46 of cover 14 just below opening 18 has a longitudinally extending shoulder or ridge to define the receiving position of tray 32, as later described.

Cover 14 also has a horizontal internal wall portion that incorporates a needle extractor 58 which extends perpendicularly into the cover interior from the base of opening 18. The needle extractor 58 is shown in FIGS. 1 and 3. Tray 32 has a wall portion 38 which in the open position of the tray (FIGS. 1, 3, and 5) is horizontal, and wall portion 38 has a cutout at one corner to provide space for the extractor 58. The needle extractor is used to hold a needle while it is being detached from its holder and thereafter permitting the needle to drop into the container without being touched, and its operation is indicated by dotted lines in FIG. 1. Preferably, the extractor is an integral component of the cover but is located such that when the container is permanently locked, the extractor is secured inside the container.

The Rotatable Tray

The rotating tray 32 is supported for rotation at its the front end by a front pivot pin 34, as best indicated in FIG. 2. The pivot pin 34 is in turn supported from the dial assembly, to be later described. A rear pivot pin 36, indicated by dotted lines in FIG. 2, engages the pivot pin recess 22 in cover 14 to pivotally support the rearward end of the tray.

Tray 32 further comprises a flat receiving member 38, a weighted member 40 weighted with a number of molded ribs 41, and a curved sliding door member 42. Receiving member 38 and weighted member 40 are joined along the pivoting axis of tray 32 and diverge from one another at an angle which is less than 180 degrees. Sliding door member 42 is joined to weighted member 40 opposite to the receiving member 38. The ribs 41 integral with weighted member 40 cause weighted member 40 to be heavier than receiving member 38. Internal wall surface portion 46 of cover 14 has a longitudinally extending shoulder or ridge to limit the upward movement of the edge of receiving member 38 so that the tray has a fixed and definite location for its open position.

In the open or receiving position of the tray the receiving wall portion 38 (see FIGS. 3 and 5) is therefore in a horizontal position and exposed to cover opening 18. The weighted wall 40 is in an inclined position relative to receiving surface 38 on the back side of the tray, and the sliding door portion 42 of the tray member 32 as shown in FIG. 5 is then hidden within the curved top of cover 14. The inclined position of weighted member 40 will then cause any object inadvertently placed on its surface to displace onto receiving member 38 by force of gravity. When member 38 is loaded and moves downward, the tray rotates, the sliding door 42 rotates into view from underneath the top of the cover, and the opening 18 which permits access to the tray is then partially obstructed, thereby reducing direct access to the container interior.

A guide bar 44 is disposed between pivot pin 34 and tray 32 on the forward end wall of cover 14 as shown in FIG. 2 and is integrally molded with the forward wall of the cover. In the receiving position of the tray the surface 38 and the guide bar 44 are each essentially in a horizontal position. The location of guide bar 44 is essential for the proper function of alignment marks 52 when the dial assembly will be used to rotate tray 32 into locking position, as will be discussed below.

Dial Assembly

A dial assembly includes a dial cup 26 having a dial cylinder receiving recess 29 on its rearward or inner side (see FIG. 2). The dial cup 26 is of generally cup-shaped configuration, has an outside diameter slightly less than the inside diameter of dial recess 20, and is rotatably supported within that recess. The depth of dial recess 20 lengthwise of the cover 14 is very small compared to the length of the cover, and the length of dial cup 26 is somewhat less than the depth of the recess 20 (see FIG. 11).

Dial cup 26 also has projecting from its rearward side an eccentric locking pin 28, a cylindrical dial member 30 which is concentric with the dial cup, and frangible connectors 31. The The dial member 30 is preferably formed integral with the cup, extending away from the back side of the cup and somewhat beyond the circumferential wall of the dial cup. More specifically, the cylindrical dial member 30 is attached to an inner wall of dial cylinder receiving recess 29 by the plurality of frangible connectors 31.

In the center of the dial member 30 there is a pivot pin opening 23, FIG. 2, which supports the forward end of the tray 32 for rotation. Dial cup 26 has a circumferential ridge 48 on its rearward end that cooperates with shoulders 50 and 56 of recess 20.

Assembly of the Apparatus

Preferably, the container, cover and tray are all molded by conventional plastic injection methods. In the most preferred embodiment, a propylene random co-polymer is used as the plastic injection material. The cover 14 is assembled in the following manner:

Tray 32 is disposed within cover 14 such that pivot pin 36 is inserted into pivot pin aperture 22 and that the edge of receiving surface 38 is below a shoulder 46 extending inward from cover 14 where it defines the base of opening 18. Receiving surface 38 has a radius distance from the pivoting axis which is less than the distance from the pivoting axis to the inside surface of cover 14 but greater than the distance from the pivoting axis to shoulder 46. When tray 32 is positioned within cover 14 and the edge of receiving surface 38 is contacting shoulder 46, weighted surface 40 is in an inclined position relative to receiving surface 38. Receiving surface 38 and guide bar 44 are essentially in a horizontal position. The position of guide bar 44 is essential for the proper function of alignment marks 52 when dial 26 will be used to rotate tray 32 into locking position as will be discussed below.

Cover 14 is permanently attached to the top of receptacle 12 using a male/female snap fit configuration, although any attachment means for permanently connecting receptacle 12 and cover 14 could be used in the alternative.

Dial 26 is inserted into dial recess 20 in a manner such that locking pin 28 is positioned below guide bar 44 and pivot pin 34 is inserted into pivot pin recess 23 of dial cylinder 30. As dial 26 is partially inserted into dial recess 20, a ridge 48 about the circumference of dial 26 is displaced past a first dial recess shoulder 50. Shoulder 50 permits movement of ridge 48 into cover 14 but prevents movement of ridge 48 in the opposite direction.

Method of Operation

The container 10 now assembled, functions in the following manner:

The additional weight on weighted member 40 from ribs 41 and sliding door 42, together with the off-center support of tray 32 from pivot pins 34 and 36, will tend to pivot tray 32 so that receiving member 38 is biased into contact with wall portion 46. An object placed upon receiving member 38 will tend to overcome the bias caused by weighted member 40 and begin to pivot receiving member 38 away from shoulder 46. As the distance between the edge of receiving member 38 and shoulder 46 increases, access for the object to the interior of receptacle 12 increases. The pivoting action will also cause gravity to displace an object toward the edge of receiving member 38 and make it eventually fall into receptacle 12. Once the object has been displaced from receiving member 38, the biasing caused by weighted member 40 will again pivot the tray 32 and receiving member 38 back into contact with shoulder 46. Additionally, while tray 32 is pivoting due to an object being deposited onto receiving member 38, sliding door member 42 is correspondingly pivoting to partially obstruct opening 18, thereby reducing the effective opening area to the inside of cover 14. This safety feature reduces the access to the interior of receptacle 12 as well as to receiving member 38 when an object is deposited thereon, thereby resisting any attempts for retrieval of disposed material.

Receiving member 38 is configured to permit direct access from needle extractor 58 to the interior of receptacle 12 when it is biased into contact with shoulder 46.

Rotational Closing of Container

Once receptacle 12 has been determined by use of viewing windows 13 to be full, container 10 is ready to be permanently and irreversibly locked prior to removal for disposal. The locking mechanism is designed so that it cannot be actuated by mistake. Two separate steps must be taken. First, the dial assembly is rotated so as both to rotate the tray 32 and sliding door 42 into a closed position, and to lock the tray against further rotation. Second, the dial assembly is forced longitudinally into the dial recess 20 of the cover 14 so that the exterior surface of the cup 26 is substantially flush with the adjacent outside end surface of the cover.

When rotating the dial cup 26 into a rotationally closed and locked position it is also necessary to apply longitudinal force to its outer end surface. The combined rotating and pushing action will then cause locking pin 28 of the dial assembly to become aligned and engaged with locking pin aperture 24 of the cover, thus preventing any rotation of the tray 32 back to the open or receiving position. The amount of rotation needed is less than ninety degrees, as is indicated by the change in angular position of the tray 32 from its FIG. 5 position to its FIG. 13 position.

The pushing action on dial cup 26 causes only a very small longitudinal movement of the tray 32, hence as shown in FIG. 7 the position of pivot pin 36 and the suspended pivot pin recess 22 relative to the end wall of cover 14 remains essentially unchanged from its position in FIG. 3.

Figure 19:
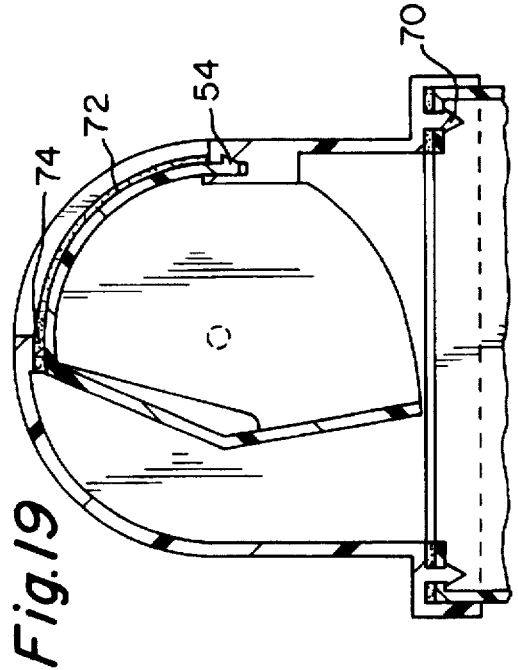
Figure 18:
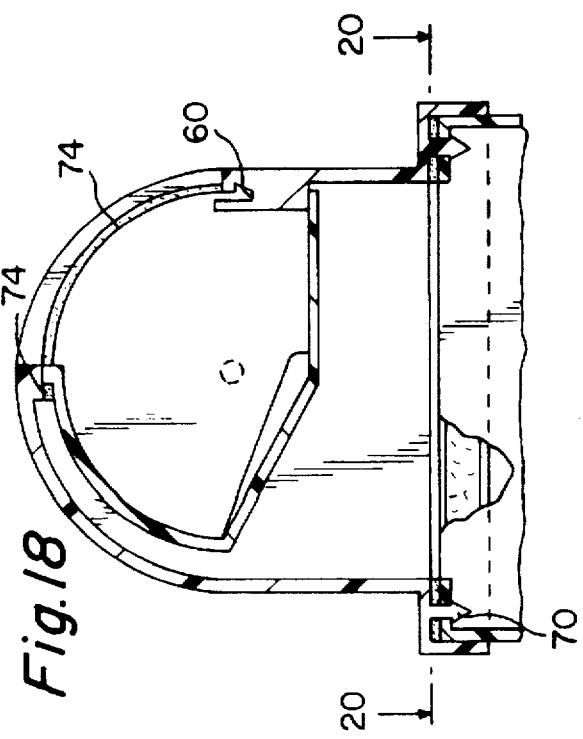
Figure 20:
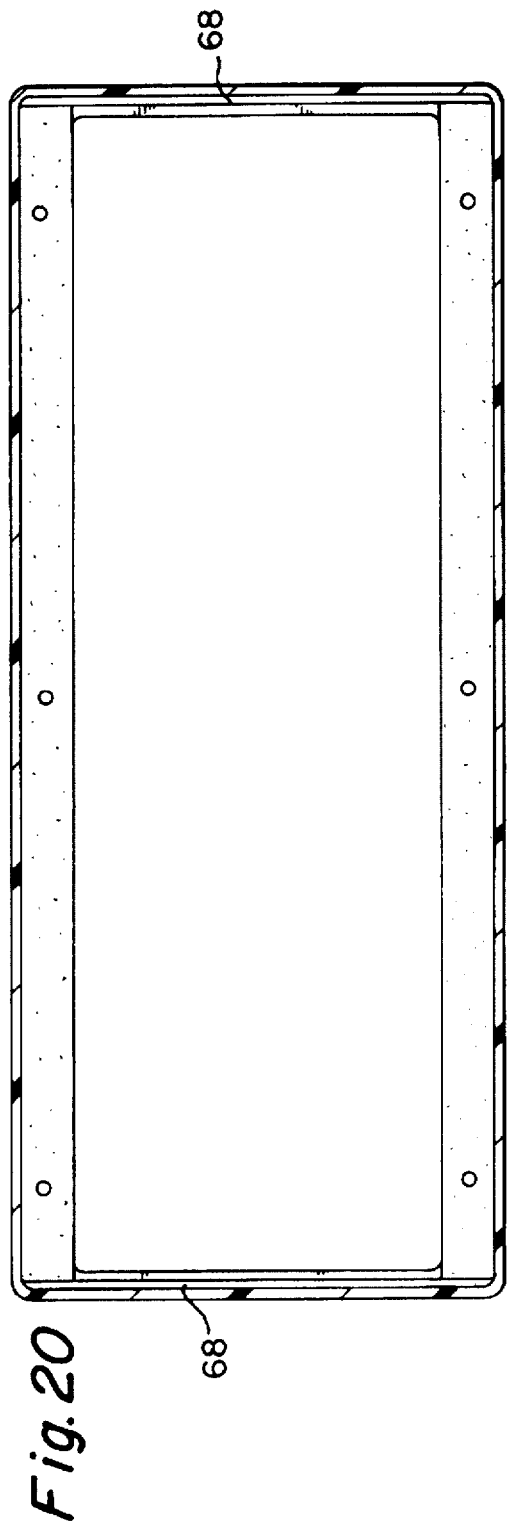

Additionally, a horizontal linear ridge 54 extending outward from the surface of sliding door 42 (shown only in FIGS. 18 and 19) will contact the inside surface of cover 14 just prior to the tray being rotated into its fully closed position. Ridge 54 will then engage with a backcut groove 60 on the inside wall of the cover, as seen in FIGS. 18 and 19. The groove 60 is integrally formed with the shoulder 46. Additional force by the operator is required to engage the linear ridge 54 with groove 60 of cover 14 and to complete the clockwise rotation of tray 32 into its fully closed and rotationally locked position.

While rotating the dial assembly, the user may hear a snapping sound as the ridge 54 becomes engaged with groove 60 of the inside cover surface. The ridge 54 now is in position to prevent rotation of the sliding door back underneath the cover to expose the cover interior. Preferably, alignment of marks 52 on dial 26 and cover 14 will inform the operator that dial 26 has been rotated into proper position. Alignment of marks 52 is indicated in FIG. 6.

Longitudinal Locking

Figure 10:
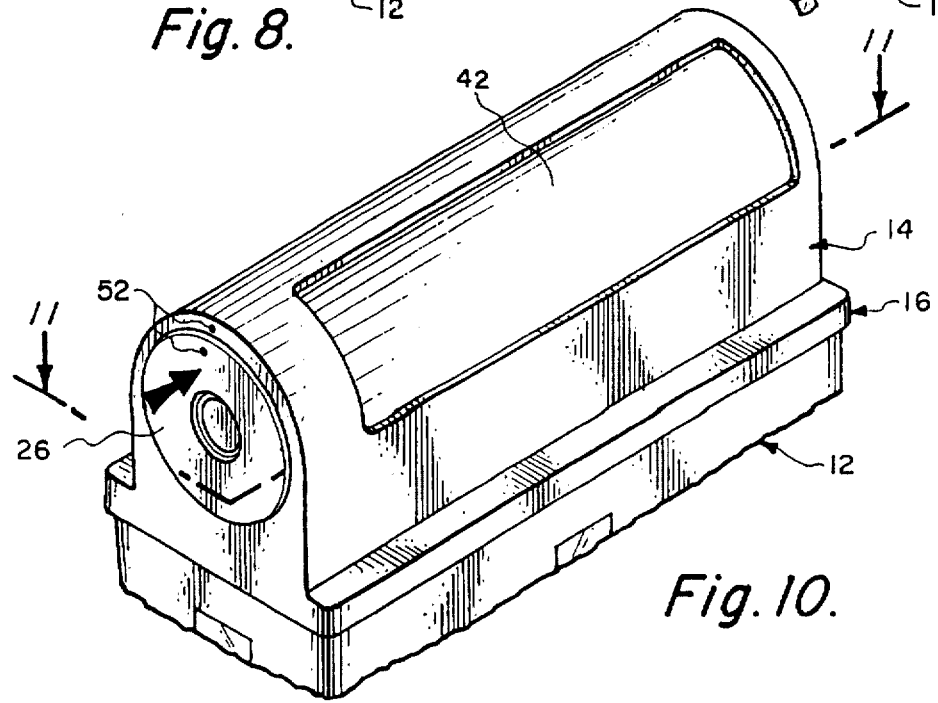
FIGS. 10 through 13 show the invention in permanently locked position.

Subsequent to dial 26 being rotated clockwise into locking position using alignment marks 52, dial cup 26 is displaced into cover 14 as is shown generally in FIG. 10. The nature of the frangible connectors is such that when the dial cylinder 30 is squeezed against the cup 26, the frangible connectors will fracture. As force is applied to displace dial cup 26 into cover 14, frangible connectors 31 fail and the connection between dial cylinder receiving recess 29 and dial cylinder 30 is severed, permitting displacement of dial cup 26 completely into dial recess 20 and corresponding displacement of dial cylinder 30 into dial cylinder receiving recess 29 and locking pin 28 into locking pin aperture 24.

During this longitudinal displacement of the dial assembly into the cover, the circumferential ridge 48 on the dial cup (see FIGS. 2 and 11) also passes the second circumferential shoulder 56 on the interior wall surface of the dial recess 20. Shoulder 56 permits movement of the dial cup and its circumferential ridge into the cover recess but prevents movement in the opposite direction. Once ridge 48 has been displaced inward past second dial recess shoulder 56, the exterior top surface of dial 26 becomes substantially flush with the adjacent exterior surface of cover 14 and is no longer accessible for manual rotation, which would in any event be prevented by the locking pin 28.

Further, the annular space or clearance between the circumferential outer surface of the dial cup 26 and inner wall surface of the dial recess 20 is minimal. The circumferential wall of dial recess 20, or the outer surface of dial cup 26, or both, is slightly tapered, so that there becomes a tighter friction fit between dial cup 26 and the wall of recess 20 as the dial cup is forced inward. As shown in FIGS. 16 and 17, an O ring 82 carried in a groove just inside the shoulder 50 not only provides a hermetic seal at that location, but also provides increased friction to prevent any disassembly of the apparatus once it has been locked.

The dial cup 26 moves inward by a distance of about a half inch, as seen from its position in FIG. 11 relative to its former position shown in FIG. 7. The position of pivot pin 36 and recess 22 are essentially unchanged during that movement of the dial cup.

Hermetic Sealing of the Container

The present invention in its preferred form provides a system of sealing mechanisms that securely and hermetically seal the container when in its locked position, so that any liquid material that may escape from a syringe or the like into the interior of the container will be securely retained there. Thus, no contaminated liquid can leak out of the interior of the container. The sealing arrangements provided are also very effective during normal operations when objects are being placed into the container for later disposal. The specific details of the presently preferred form of sealing arrangement are shown in FIGS. 14 through 20.

A flat strip of sealing material 68 extends in a rectangular pattern about the upper periphery of the receptacle 12 and is compressively engaged by the lower periphery of the cover 14. Hooks 70 (FIGS. 18 and 19) extend down from the cover and ensure continued pressure on the sealing member.

Tray 32 has a layer of sealing material 72 on its outer periphery along the two end edges and its top edge (see FIGS. 14 and 15) which hermetically seals those three joints to the cover 14 when the tray is in its rotationally locked position. Above the tray, a layer of sealing material 74 is placed underneath the inner edge surface of cover 14 at the upper boundary and sides of opening 18 (FIGS. 18 and 19).

When the tray is in its rotationally locked position, the forward lower edge of sliding door member 42 is sealed by the ridge 54 and groove 60, as previously described. Because of the nature of the plastic material employed, the snap fit of these two members provides a hermetic seal.

The outer circumference of dial cup 26 is sealed by an O ring 80, which is actually supported from the wall of dial recess 20 just inside the shoulder 50 (FIG. 19). As earlier described, there is an increasingly tight friction fit as the dial cup enters the recess.

An O ring 82 is provided around the outer circumference of dial member 30 (FIGS. 16 and 17). A flat circular compression sealing member 84 abuts the inner end surface of dial member 30.

The engagement of pivot pin 34 into recess 23 of dial member 30 (FIGS. 16 and 17) also provides a hermetic seal, again because of the nature of the plastic material employed and a snap fit of these two members.

Although not specifically shown in the drawings, a set of two or more hooks protruding longitudinally outwardly from the circumferential wall of the dial cup 26 is provided, so that a hook-and-latch type of connection can be made with associated openings in wall 25 of cover 14, in the same manner as the hook-and-latch attachment at the bottom of the cover, as shown in FIGS. 18 and 19.

While the presently preferred form of the invention has been disclosed in detail in order to comply with the requirements of the patent laws, it will be understood the scope of the invention is to be judged only by the appended claims.

What we claim is:

1. In a sharps disposal container, the combination of a receptacle and cover wherein the receptacle is of generally box-like configuration having an open top; the cover is of a horizontally extending, generally semi-cylindrical configuration, and has a horizontal base for attachment to the top of the receptacle; the base of the cover and the upper perimeter of the receptacle are provided with interlocking edges so that once assembled they are permanently locked together; the receptacle has side walls with viewing windows made of a puncture resistant material; the cover has a side wall with an elongated opening formed therein; one end wall of the cover has a dial recess formed therein; and the other end wall of the cover has a pivot pin recess formed therein for rotatably supporting one end of a rotatable tray that may be positioned within the cover and accessible through the elongated opening.

2. A sharps disposal container as in claim 1 which further includes a dial assembly located within the dial recess, an elongated rotatable tray located within the cover, and one end of the tray being rotatably supported from the pivot pin recess while the other end is pivotally supported from the dial assembly.

3. A sharps disposal container as in claim 2 wherein the tray comprises a flat receiving member, a weighted member, and a curved sliding door member, the receiving member and weighted member being joined along a pivoting axis of the tray and diverge from one another at an angle which is less than 180 degrees, and the sliding door member being joined to the weighted member opposite to the flat receiving member.

4. A sharps disposal container as in claim 2 wherein the dial assembly includes a dial cup of generally cup-shaped configuration rotatably supported within the dial recess, having a bottom wall facing outwardly from the dial recess, and the dial cup having a dial receiving recess on its inner side facing inwardly of the cover.

5. A sharps disposal container as in claim 4 wherein the dial cup has projecting from its rearward side an eccentric locking pin which is adapted to selectively engage an opening in one end of the tray for drivingly rotating the tray into a locked position.

6. A sharps disposal container as in claim 5 which further includes a cylindrical dial member concentrically disposed within the dial receiving recess of the dial cup and is with the dial cup, and frangible connectors securing it to the dial cup.

7. A sharps disposal container as in claim 1 having means hermetically sealing the receptacle and the cover together.

8. In a sharps disposal container, an elongated tray adapted to be rotatably supported about a longitudinal axis and comprising a flat receiving member, a weighted member, and a curved sliding door member, the flat receiving member and the weighted member being joined along the pivoting axis of the tray and diverging from one another at an angle which is less than 180 degrees, the sliding door member being joined to the weighted member opposite to the receiving member, and the weighted member being heavier than the flat receiving member such that the flat receiving member, in the absence of a vertical restraint on its outer edge, would not normally lie in a horizontal position.

9. A sharps disposal container as in claim 8 which includes a hollow cover within which the elongated tray is disposed, and wherein an internal wall surface portion of the cover has a longitudinally extending shoulder formed thereon to limit the upward movement of the edge of the flat receiving member.

10. A sharps disposal container as in claim 8 having means on the exterior edge surfaces of the tray for hermetically sealing it within a container.

11. In a sharps disposal container, a dial assembly including a dial cup having its open end forming a dial cylinder receiving recess, the dial cup being of generally cup-shaped configuration, an eccentric locking pin projecting from the dial cylinder receiving recess, a cylindrical dial member occupying the dial cylinder receiver recess concentric with the dial cup, and frangible connectors securing the cylindrical dial member to an inner wall of the dial cylinder receiving recess.

12. A sharps disposal container comprising a receptacle, a cover having an opening for receiving items to be disposed, an elongated tray rotatably supported within the cover and accessible to the opening, hand-operated rotatable means associated with the cover and coupled to the tray for selectively rotating the tray to a closed position in which a portion of the tray closes the opening, hand-operated means adapted to be forced into a recess in the cover for locking the tray in its closed position, and hermetic sealing means for hermetically sealing the cooperating surfaces of the receptacle, the cover, and the hand-operated means.

13. A sharps disposal container as in claim 12 wherein the hand-operated rotatable means in also the means adapted to be forced into a recess in the cover.

14. A sharps container comprising:
a receptacle for receiving sharps;
a cover connected to said receptacle in such a manner as to define an inner space between the receptacle and the cover, the cover further having a dial recess and an opening for receiving sharps into the receptacle;
a dial assembly partially disposed within the dial recess, moveably and rotatably mounted to the cover;
an elongated tray disposed in the cover, the tray being rotatable about a horizontal axis between receiving, partially closed, and locking positions, said receiving position being adapted for receiving sharps through said opening while closing access to said receptacle interior, said tray being biased into said receiving position and overcoming said bias to rotate to a partially closed position when an object is placed onto said tray, said tray then rotating in a direction opposite of said bias into said partially closed position until said object falls by force of gravity into said interior, whereupon said tray automatically rotates back to said receiving position;
means responsive to manual rotation of the dial assembly for securing said tray in said locking position; and
said tray and dial assembly being supported by sealing means which provide a hermetically sealed interior when said tray is in said locking position, thereby preventing leakage of fluids from the interior of said container.

15. A sharps container as recited in claim 14 wherein said receptacle further comprises a viewing window to permit visual inspection of the interior of said receptacle.

16. In a sharps container having a receptacle and a cover with an opening therein, and an elongated tray rotatably supported beneath said opening, the improvement comprising:
means biasing said tray to a normal receiving position for receiving sharps onto said tray through said opening and to restrain communication of sharps directly into said receptacle;
the longitudinal support of said tray being biased by a sufficient offset from said opening so that when a sharps is deposited onto said tray, said tray rotates and allows the sharps to enter the receptacle and correspondingly, said tray, as it rotates counter to said biasing means, partially obstructs said opening to said container thereby restricting access to the interior of said container, and then, responsive to said biasing means, returns to its normal receiving position; and said tray being supported by sealing means which provide a hermetically sealed interior when said tray is in said locking position, thereby preventing leakage of fluids from the interior of said container.

17. In a sharps container having a receptacle, a cover with an opening therein, an elongated tray rotatably supported beneath said opening, and a means connected to said container for assisting the rotation of said tray, the improvement comprising:

a locking means for selectively and permanently locking said tray in a locking position and thereby closing said container, said locking means, when actuated, displacing said tray rotation assist means into said cover so that the exterior of said tray rotation assist means is substantially flush with the adjacent exterior surface of said cover; and said tray and cover being having cooperating sealing means which provide a hermetically sealed interior when said tray is in said locking position, thereby preventing leakage of fluids from the interior of said container.

18. The improvement as recited in claim 17 where said locking means comprises a dial assembly partially disposed within a dial recess located in said cover and moveably and rotatably connected to said cover, a locking pin receiving aperture located in said cover, a locking pin which extends from said dial assembly and which is movable between a first position wherein said locking pin is removed from said locking pin receiving aperture and a second position wherein said dial is manually moveable into locking engagement with said dial recess thereby moving said locking pin into said locking pin receiving aperture when said tray has been rotated into said locking position.

* * * * *